United States Patent
Kälberer et al.

[11] Patent Number: 5,879,397
[45] Date of Patent: Mar. 9, 1999

[54] TAPERED HIP JOINT SOCKET

[75] Inventors: Hartmut Kälberer, Deizisau; Hans-Georg Pfaff, Ostfildern, both of Germany

[73] Assignee: Cerasiv, GmbH Innovative Keramik Engineers, Plochingen, Germany

[21] Appl. No.: 324,264

[22] Filed: Oct. 17, 1994

[30] Foreign Application Priority Data

Oct. 21, 1993 [DE] Germany ............ 43 35 931.0

[51] Int. Cl.$^6$ .................................. A61F 2/32
[52] U.S. Cl. ................................. 623/22; 623/18
[58] Field of Search ................ 623/16, 18, 20, 623/22, 23

[56] References Cited

U.S. PATENT DOCUMENTS

| | | | |
|---|---|---|---|
| Re. 28,895 | 7/1976 | Noiles | 623/22 |
| Re. 31,865 | 4/1985 | Roux | 623/22 |
| 4,180,873 | 1/1980 | Fixel. | |
| 4,566,138 | 1/1986 | Lewis et al. | 623/22 |
| 4,813,959 | 3/1989 | Cremascoli | 623/22 |
| 5,263,988 | 11/1993 | Huebner | 623/22 |
| 5,282,864 | 2/1994 | Noiles et al. | 623/18 |
| 5,376,122 | 12/1994 | Pappas et al. | 623/22 |

FOREIGN PATENT DOCUMENTS

| | | |
|---|---|---|
| 0083708 | 7/1983 | European Pat. Off. . |
| 0142959 | 5/1985 | European Pat. Off. . |
| 0162005 | 11/1985 | European Pat. Off. . |
| 0482320 | 4/1992 | European Pat. Off. . |
| 2598609 | 11/1987 | France . |
| 2628315 | 9/1989 | France . |
| 2682588 | 4/1993 | France . |
| 677072 | 4/1991 | Switzerland . |

*Primary Examiner*—David Isabella
*Attorney, Agent, or Firm*—Fulbright & Jaworski

[57] ABSTRACT

Disclosed is a hip joint socket for insertion into bone tissue, having an outer metal shell and an inner antifriction liner. The antifriction liner is fixed in the metal shell by means of a taper lock. To safeguard the socket insert and antifriction liner against misalignment and separation, and enable a non-destructive removal of the liner and replacement thereof, the angle ($\alpha$) of the taper lock of the liner in the shell is between 10° and 25°.

5 Claims, 1 Drawing Sheet

TAPERED HIP JOINT SOCKET

BACKGROUND OF THE INVENTION

The invention relates to a hip joint socket for insertion into bone tissue.

Hip joint endoprostheses consist of a hip joint socket which is anchored in the pelvic bone and a ball, which is inserted into the socket for rotation therein, and is anchored to a shaft in the femur.

Hip joint sockets consist of an outer metal shell which constitutes the external shape of the implant, and an inner antifriction liner which is made of ceramic or of plastic such as an ultra-high molecular weight polyethylene (UHMWPE).

It is state of the art to fix the antifriction liner in the metal shell by means of a taper lock having an angle of about 5° 43', i.e., an angle ratio of 1:10. A disadvantage of this socket is that the antifriction liner easily becomes canted when inserted into the metal shell resulting in an unequal distribution of forces which, under some circumstances, can result in a fracture of the internal antifriction liner especially if it is made of ceramic. Another important disadvantage is that after the antifriction liner or socket has been installed, the antifriction liner can no longer be removed nondestructively due to the high seizing forces. However removeability without destruction is extremely important for the surgeon. A further disadvantage is that due to the configuration of the antifriction liner and socket insert the overall size of the implant has to be made relatively large. This is a disadvantage from the medical viewpoint because either it entails significant bone loss or, if the bone wall is thin, may prevent installation of such an implant.

SUMMARY OF THE INVENTION

The present invention provides an improved hip joint socket for insertion into bone tissue such that the socket insert and antifriction liner is safeguarded against misalignment and separation. Further, the present invention provides a socket wherein the antifriction liner is replaceable and is removable without damage.

The various features of novelty which characterize the invention are pointed out with particularity in the claims annexed to and forming a part of this specification. For a better understanding of the invention, its operating advantages and specific objects obtained by its use, reference should be made to the accompanying drawings and descriptive matter in which there is illustrated and described a preferred embodiment of the invention.

DESCRIPTION OF PREFERRED EMBODIMENT

The present invention overcomes the prior art drawbacks in that the angle of the taper lock of the antifriction liner in the shell is between 10° and 25°. In a preferred embodiment, the angle of the taper lock is about 18°.

Due to the selection according to the invention of the angle of the taper lock, the socket and antifriction liner are safeguarded against misalignment and separation. However, a special advantage of the invention resides in the fact that the force required for removing the antifriction liner out of the metal shell is substantially less than in the state of the art. In the case of the preferred taper lock angle of 18° the force required for removal of the liner is approximately only half of the insertion force. Thus the disengaging moment is less.

For equal antifriction liner wall thickness, the force-transmitting surface area is greater than in the conventional 1:10 taper lock. Consequently the antifriction liner and socket insert have greater mechanical strength. Thus to provide equal strength to the prior art structure, the socket of the invention can be made smaller and more shallow satisfying the medical need for small implants.

The preferred external angle of 18° thus achieves several advantages.

Figure 1:
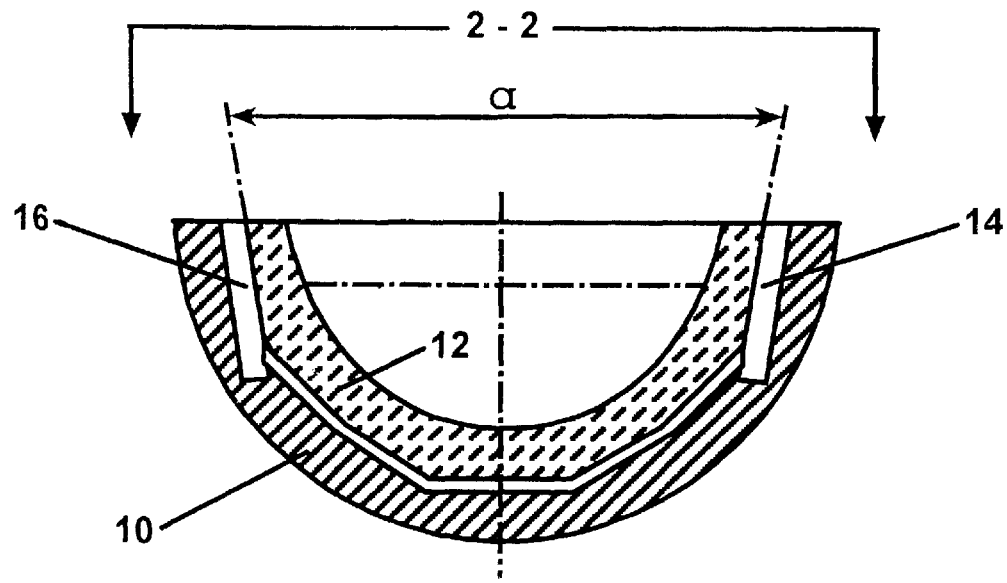
FIG. 1 shows a cross section of a hip joint socket according to the invention.
Figure 2:
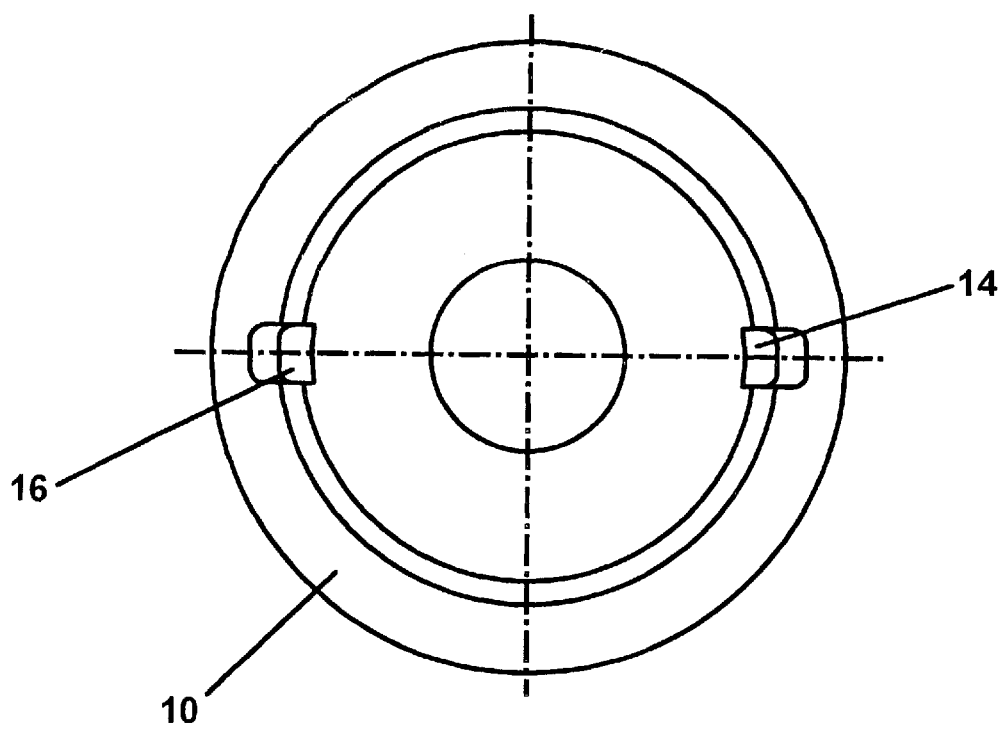
FIG. 2 is a view along view line 2—2 of the hip joint socket of FIG. 1 with liner 12 removed.

To enable the antifriction liner to be pried out, at least one recess is disposed advantageously in the contact area between the metal shell and the antifriction liner. As shown in FIG. 1, the recess extends to a depth below the section of the shell having the taper angle $\alpha$. In a preferred embodiment, two such diametrically opposite recesses are provided. To pry out the antifriction liner, an extraction tool, in the shape, for example, of a golf club, is inserted into the recess. Turning the tool generates a force from below against the antifriction liner, which is thus easily released from its taper lock. Removal of the liner is facilitated if two prying tools are introduced into two diametrically opposite recesses and turned simultaneously, so that the antifriction liner can be forced simultaneously on two sides in the extracting direction.

The low disengaging forces make it possible to design small extraction tools. As a result, the outside dimension of the implant can be made small, because the recesses through which the extraction tools are guided can be made small.

In accordance with the invention the antifriction liner is preferably made of ceramic.

Referring to the figures, the external shape of the implant is formed by a metal shell 10. Antifriction liner 12 is of a ceramic material and is inserted into metal shell 10 such that the top edge of the shell and of the antifriction liner 12 are at the same level. The liner 12 is fixed in the metal shell by a taper lock. According to the invention the angle $\alpha$ of the taper lock is between 10° and 25°; and, in a preferred embodiment is about 18°.

Antifriction liner 12 is inserted into the shell 10 by placing the liner 12 in the metal shell and then forcing the liner into the shell. The liner 12 may be inserted into shell 10 by i.e. hammering, through a wood block. To remove the antifriction liner 12, two diametrically opposite recesses 14 and 16 are disposed in accord with the invention in the metal shell 10 on the surface of contact with the antifriction liner 12. An extraction tool (not shown) is introduced into each of recesses 14 and 16 and turned simultaneously, so that pressure is exerted from below from two sides in the direction of extraction.

The hip joint socket according to the invention has the advantage that the antifriction liner 12 is tightly anchored in the metal shell 101 but can easily be removed even when the shell is already implanted, i.e., during an operation. Furthermore, the hip joint socket is small in size.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What is claimed is:

1. A hip joint socket for insertion into bone tissue, comprising: an outer metal shell; and an inner antifriction liner of a ceramic material removably fixed in the metal shell solely by means of a taper lock having a taper lock angle ($\alpha$) of from 10° to 25°.

2. The hip joint socket of claim 1 wherein the angle ($\alpha$) of the taper lock is about 18°.

3. The hip joint socket of claim 1 wherein the metal shell on the surface of contact with the antifriction liner is adapted with at least one recess disposed to enable removal of the antifriction liner.

4. The hip socket of claim 3 having two diametrically opposite disposed recesses.

5. A hip joint socket for insertion into bone tissue, comprising: an outer metal shell and an inner antifriction liner removably fixed in the metal shell solely by means of a taper lock having a taper lock angle ($\alpha$) angle of from 10° to 25° wherein the metal shell on the surface of contact with the antifriction liner is adapted with at least one recess disposed to enable removal of the antifriction liner.

* * * * *

UNITED STATES PATENT AND TRADEMARK OFFICE
CERTIFICATE OF CORRECTION

PATENT NO. : 5,879,397
DATED : March 9, 1999
INVENTOR(S) : Kalberer, et. al.

It is certified that error appears in the above-identified patent and that said Letters Patent is hereby corrected as shown below:

Title page, under Foreign Patent Documents, line 2, change "0142959" to --0142759--.

Signed and Sealed this

Eleventh Day of July, 2000

*Attest:*

Q. TODD DICKINSON

*Attesting Officer*      *Director of Patents and Trademarks*

(12) EX PARTE REEXAMINATION CERTIFICATE (6396th)
United States Patent
Kälberer et al.

(10) Number: US 5,879,397 C1
(45) Certificate Issued: Aug. 26, 2008

(54) TAPERED HIP JOINT SOCKET

(75) Inventors: Hartmut Kälberer, Deizisau (DE); Hans-Georg Pfaff, Ostfildern (DE)

(73) Assignee: Cerasiv GmbH, Innovatives Keramik-Engineering, Plochingen (DE)

Reexamination Request:
No. 90/005,914, Jan. 25, 2001

Reexamination Certificate for:
Patent No.: 5,879,397
Issued: Mar. 9, 1999
Appl. No.: 08/324,264
Filed: Oct. 17, 1994

Certificate of Correction issued Jul. 11, 2000.

(30) Foreign Application Priority Data

Oct. 21, 1993 (DE) .......................................... 43 35 931

(51) Int. Cl.
*A61F 2/32* (2006.01)
*A61F 2/46* (2006.01)
*A61F 2/34* (2006.01)
*A61F 2/30* (2006.01)
*A61F 2/00* (2006.01)

(52) U.S. Cl. ................................. 623/22.25; 623/22.28
(58) Field of Classification Search ....... 623/22.2–22.46
See application file for complete search history.

(56) References Cited

U.S. PATENT DOCUMENTS

| | | | |
|---|---|---|---|
| 4,566,138 A | 1/1986 | Lewis et al. | |
| 4,813,959 A | 3/1989 | Cremascoli | |
| 5,263,988 A | 11/1993 | Huebner | |
| 5,282,864 A | 2/1994 | Noiles et al. | |
| 5,413,603 A | 5/1995 | Noiles et al. | |

*Primary Examiner*—Bruce E. Snow

(57) ABSTRACT

Disclosed is a hip joint socket for insertion into bone tissue, having an outer metal shell and an inner antifriction liner. The antifriction liner is fixed in the metal shell by means of a taper lock. To safeguard the socket insert and antifriction liner against misalignment and separation, and enable a non-destructive removal of the liner and replacement thereof, the angle ($\alpha$) of the taper lock of the liner in the shell is between 10° and 25°.

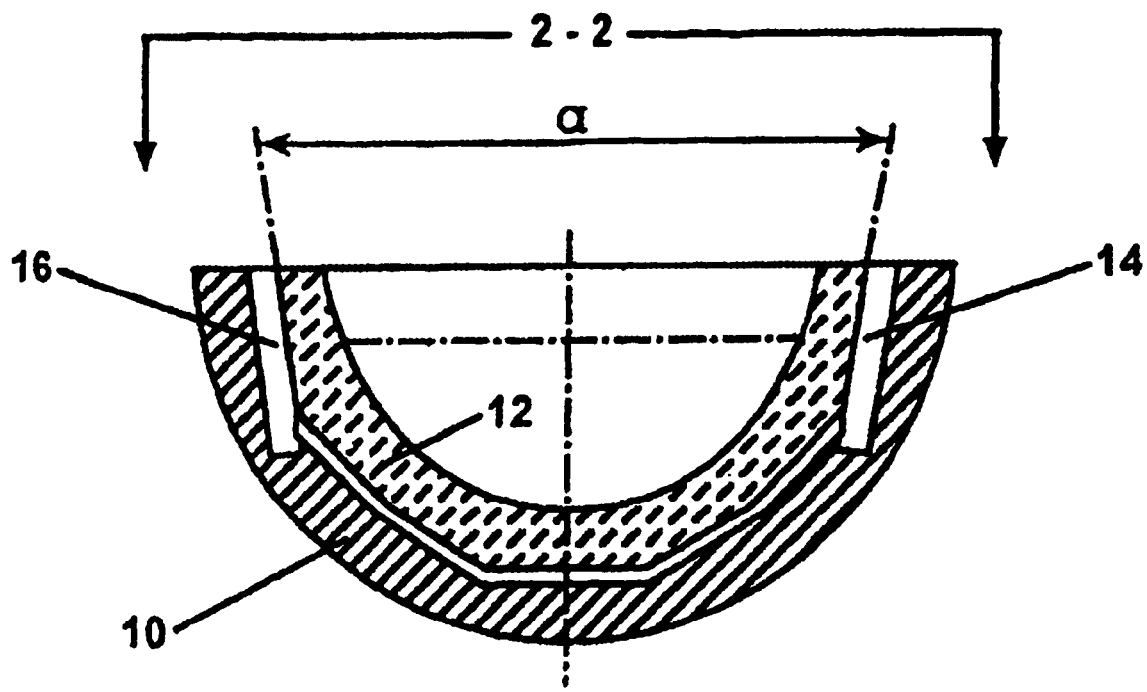

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–5 are cancelled.

\* \* \* \* \*